(12) United States Patent
Haider et al.

(10) Patent No.: US 7,602,953 B2
(45) Date of Patent: Oct. 13, 2009

(54) METHOD FOR ACQUISITION, ANALYSIS AND REPRESENTATION OF A MEDICAL IMAGE DATA SET

(75) Inventors: Sultan Haider, Erlangen (DE); Axel Schreiber, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 236 days.

(21) Appl. No.: 11/449,531

(22) Filed: Jun. 7, 2006

(65) Prior Publication Data
US 2006/0285734 A1     Dec. 21, 2006

(30) Foreign Application Priority Data
Jun. 7, 2005     (DE) .................. 10 2005 026 220

(51) Int. Cl.
*G06K 9/00*     (2006.01)
(52) U.S. Cl. ................. 382/128; 706/2; 706/3; 706/4; 382/130; 382/131; 715/214; 715/275
(58) Field of Classification Search ................ 382/128; 705/2–4; 715/214, 275
See application file for complete search history.

(56) References Cited

U.S. PATENT DOCUMENTS

| | | | | |
|---|---|---|---|---|
| 5,218,623 A | * | 6/1993 | Toki et al. ................ 378/4 |
| 5,454,019 A | * | 9/1995 | Migita et al. ............. 378/15 |
| 5,668,846 A | * | 9/1997 | Fox et al. ................ 378/4 |
| 6,023,495 A | * | 2/2000 | Adler et al. .............. 378/4 |
| 6,195,409 B1 | * | 2/2001 | Chang et al. ............. 378/20 |
| 6,896,657 B2 | * | 5/2005 | Willis .................... 600/437 |
| 2002/0198447 A1 | * | 12/2002 | Van Muiswinkel et al. .. 600/410 |
| 2003/0144589 A1 | * | 7/2003 | Roell .................... 600/410 |
| 2004/0264756 A1 | * | 12/2004 | Spahn ................... 382/132 |
| 2006/0010013 A1 | * | 1/2006 | Yamatake ................ 705/2 |

FOREIGN PATENT DOCUMENTS

DE     103 46 410     5/2005

\* cited by examiner

*Primary Examiner*—Brian Casler
*Assistant Examiner*—Baisakhi Roy
(74) *Attorney, Agent, or Firm*—Schiff Hardin LLP

(57) ABSTRACT

In a method for acquisition, analysis and representation of at least one medical image data set created in a medical examination, an image data set of an examination region of an examination subject is acquired with a medical imaging apparatus, at least one display specification regarding an orientation to be retained in a graphical representation of the acquired image data set is retrieved from a data processing device in which it is stored, the image data set is checked with regard to the display specification by the data processing device, and of at least one part of the image data set is adapted and displayed corresponding to the display specification, dependent on the check result.

20 Claims, 3 Drawing Sheets

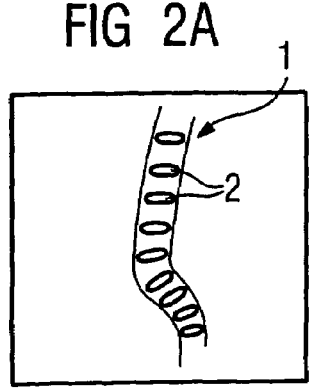
FIG 2A
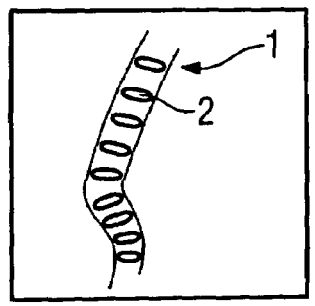
FIG 2B
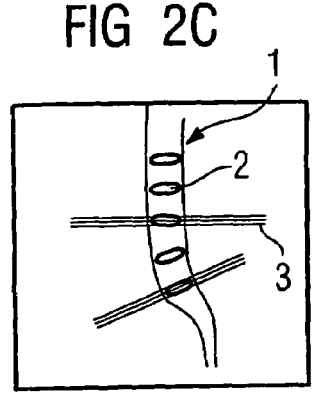
FIG 2C
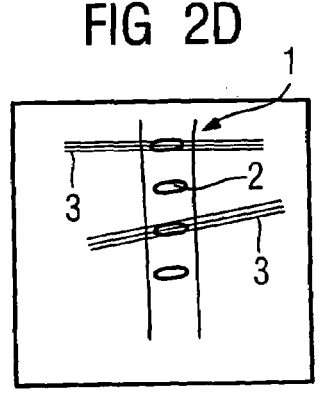
FIG 2D
FIG 2E
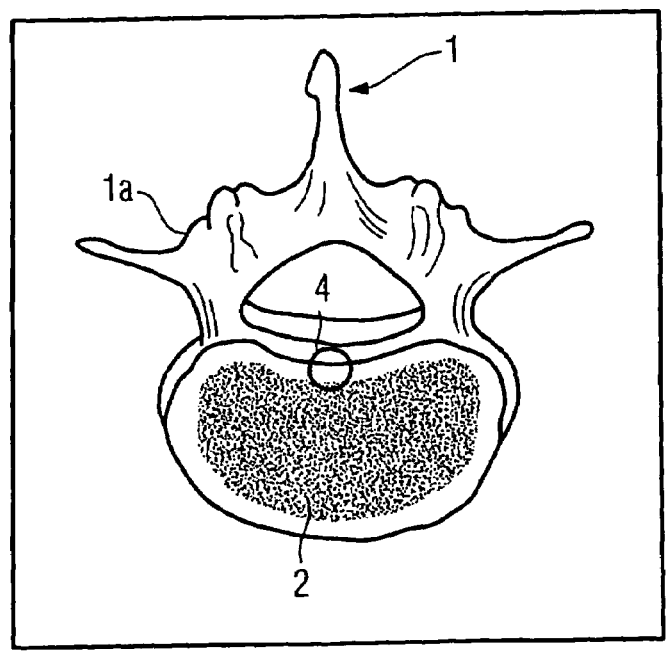

METHOD FOR ACQUISITION, ANALYSIS AND REPRESENTATION OF A MEDICAL IMAGE DATA SET

BACKGROUND OF THE INVENTION

1. Field of the Invention

The present invention concerns a method for acquisition, analysis and representation of at least one medical image data set to be created in the examination of a subject.

2. Description of the Prior Art

In medical imaging, the image orientation and position are generally determined by the type and manner of the image acquisition, thus by geometric measurement parameters or the patient position or by parameters that are used for the image reconstruction. In the context of the image reconstruction, the tomographic sections of the subject are ultimately determined that are stored in a databank, for example a central image archive.

If the images are subsequently viewed, this normally ensues with the same sequences as they are stored in the databank. This means that, after the loading of an image series into an image display (such as a computer or monitor), initially the first image or in some cases initially a middle image is shown. This can lead to the situation, for example in the imaging representation of a sagittal acquisition series of the spinal column, that the first section shows the foramina of the spinal column to the left while, in a second series (for example in the context of a subsequent examination), the first image shows the right-side foramina. Also, if there is a standardized workflow for medical assessment of image exposures of specific examination regions in an examination apparatus, it is necessary for the examiner to initially search the image exposure series in order to find the standard starting point. In the implementation of subsequent examinations, or in general in a comparative evaluation, the problem is further exacerbated because, when two image series are loaded from an image archive, the two image series both showing the same organ, normally a different view of this organ is shown in each series, such that (for example given a spinal column exposure) the left-side foramina are shown and, in another series, the right-side foramina are shown. This makes the evaluation of comparative studies and subsequent examinations not only very difficult and cumbersome to implement, but also the efficiency suffers, such that under the circumstances the quality of the diagnostic evaluation decreases.

SUMMARY OF THE INVENTION

An object of the present invention is to provide a method for acquisition, analysis and representation of medical images that is improved with regard to and to the above-discussed aspects, which enable a reliable evaluation of comparative studies.

This object is achieved in accordance with invention by a method wherein an image data set of an examination region of an examination subject is acquired with a medical imaging apparatus, at least one display specification regarding an orientation to be retained given a graphical representation of the acquired image data set is retrieved from a data processing device in which the display specification is stored. The image data set is checked with regard to the display specification by the data processing device, and at least one part of the image data set is adapted and displayed corresponding to the display specification, dependent on the check result.

According to the invention, an image data set is initially acquired with a medical imaging apparatus such as, for example, a magnetic resonance apparatus, a computed tomography apparatus, an x-ray apparatus or an ultrasound apparatus. Furthermore, a display specification stored in a data processing device is accessed. This storage can occur when an image representation is desired, but may have already occurred during the image acquisition or even in advance of an image acquisition. The display specification can be stored in a data processing device that is directly connected with an examination apparatus, for example for control thereof. The data processing device can be a computer system, for example formed by one or more servers and clients that are connected via a network, with the display specifications (in addition to other data) being stored in a central server or in a server associated with a special processor for use in the image processing.

The display specification that is retrieved by the data processing device is in regard to an orientation to be retained in the sense that, for example, the positioning of a specific anatomical structure is predetermined in the image or in a series of multiple images or partial image series. the display specification thus can be a standard format with regard to the image orientation.

The acquired image data set can be an image data set that contains one image or a series of images or even image sequences. This image data set is checked by the data processing device with regard to the display specification. It is thereby established whether the image data set already exhibits the orientation of the display specification to be maintained and if not, which deviations from the display specification exist, for example with regard to the region shown in individual images, or, a displacement or rotation with regard to the desired orientation. In the checking it may be recognized that some data that, for example, correspond to the individual images of the image data set should be directly excluded for a representation (for example the first images of an image series or the last images of a series) without the actual content of the individual images being taken into account for the check.

After the checking step, the adaptation and representation of at least one part of the image data set corresponding to the display specification ensues on an image display (such as a monitor or a display) dependent on the result of the check. The adaptation can be implemented such that the original image data are appropriately replaced by the display specification. A standardized representation is thus possible with the inventive method.

It is also possible that the originally-acquired data are appropriately retained, for example for further processing for comparison with another exposure series in which a different display specification would be to be considered under the circumstances. Furthermore, it is useful to archive the original image data in order, if necessary, to be able to reproduce the individual steps of the evaluation and diagnostics and to be able to also detect errors after the event. A portion of the image data or even the entire image data set is shown depending on the content of the display specification that, for example, can designate that only a few centimeters to the right and left of the body center should be sagittally displayed from an image series that covers the entire body trunk.

In contrast to conventional approaches for image representation, it is thus possible to enable a standardized medical assessment and a standardized evaluation of image data, in particularly in the case of comparative studies. It is no longer necessary to seek or to define anatomically-related starting images, as would otherwise be necessary given different orientations of the image exposures. Moreover, complicated algorithms in order to find such start images are avoided. The load time for the viewing via an image display means can thus be reduced, or the time for manual searching of start images can be saved. The diagnosis can be efficiently implemented without quality losses.

According to the invention, a display specification specific for the examination region (in particular a display specification specific for an acquired organ) can be used. It thus makes sense to store for retrieval respective standardized orientation formats for all organs expected to the subject of image acquisitions with medical apparatuses, or at least the most important organs examined with specific examination apparatuses. the brain, the spinal column with its individual segments, the heart, the knee and further bone structures as well as organs such as the lungs and even the vascular system are examples. This list should be understood as non-exclusive; rather, it decidedly depends on which examinations are predominantly implemented, or to be implemented at all, in a specific medical facility (such as a clinic).

Multiple representation parameters, in particular a fundamental representation parameter and further supplementary parameters, can be predetermined as display specifications. For example, a simple display specification for the lumbar spinal column can establish that sagittal image exposures are, in principle, shown in parallel to the longitudinal axis of a vertebra, or the spinal column. A different fundamental representation parameter can designate that the spinal column is, in principle, shown in the image center.

Supplementary representation parameters can specify that the longitudinal axis of the spinal column in the image should be shown from the top to the bottom, thus parallel to the image border, and the first image to be displayed should be the sagittal image that proceeds through the right-left center of the spinal column. Furthermore, representation parameters can be predetermined that specify where a specific vertebra or (for other organs) where a specific anatomical structure should appear in the image, or how an alignment oriented on the body axes is to be interpreted with regard to the examination region.

In accordance with the invention, multiple display specifications (particularly a number of display specifications specific to an examination region) can be stored in the data processing device. Display specifications for a number of examination regions or for a number of typical image exposure series can thus be stored in the data processing device and, if applicable, be retrieved from the data processing device multiple times. Multiple display specifications can be ready for retrieval for one of these examination regions dependent on the goal of an image acquisition or the acquisition technique. For example, the situation can be accommodated of, dependent on the acquisition technique, different image data sets being acquired for use with different examination apparatuses, these image data sets possibly requiring different display representations for an evaluation thereof. The display specifications, however, also can be user-specific in order to satisfy different desires with regard to an image representation as are, for example, preferred by different departments of the medical facility or even by individual doctors. Depending on the goal of the examination or depending on the underlying pathology, it is useful (for example for images of the spinal column) to provide sagittal images as standard orientations and as well as axial images that proceed parallel to the plane through the intervertebral discs (and possibly further sections, such as coronal images). For example, for cardiac exposures, views of the short axis, two chamber views as well as four chamber views can be provided as display specifications.

According to the display specification, a representation of an anatomical region of interest can be effected centrally with regard to a display region provided by an image display unit. Insofar as no other representation is explicitly defined, this central representation can be considered as a default specification that initially provided an access to the representation of the anatomical region of interest such as, for example, a specific organ (for example, with regard to further image exposures to be shown subsequently or with regard to processing by a medical-technical assistant or a doctor).

A representation instruction specifying the relationship between the coordinates of the acquired image data set and the coordinates of an image data set that is adapted to the display specification can be determined by means of the data processing device. This representation instruction, which is calculated by a computer, or a network of computers, of the data processing device, describes the coordinate transformation that is to be implemented in order to arrive at the coordinate set forming the basis of the representation from the original coordinates of the image data set. If this transformation is implemented, it proceeds from the original image data set to the standard format of the orientation as specified in the display specification for the representation of the acquired examination region. A maximum of three translation transformations and three rotation transformations can be provided, for example by specification of the coordinates of the representation center of the examination region or organs and three angles or a 4×4 transformation matrix. Alternatively, fewer parameters can be determined or stored as a representation instruction for a transformation to be implemented, for example only one or two parameters. The use of one parameter could merely specify which section should be shown first. The representation instruction is understood as an arbitrary specification that describes the relationships between the acquired image data set and the adapted image data set.

According to the invention, the display specification and/or the representation instruction can be determined automatically, at least in part, by the data processing device using examination region-specific and/or organ-specific and/or examination apparatus-specific and/or general image processing techniques and/or predetermined rules. For example, atlas-based methods can be used that are based on statistical specifications regarding anatomical or functional interrelationships in the human body and are thus specific for particular examination regions. For magnetic resonance tomography, an extraction of the organ contour using a projection oriented to the maximum signal intensity can be used for the determination of a representation instruction. In computed tomography, values for intensity standards can be used given radiation values that are specific to positron emission tomography. Furthermore, new display specifications can be created or representation instructions for the transformation between the original image data and the representation view of the adapted image data can be determined using general image processing techniques for finding specific structures. Examples are the use of adaptive filters, specific models for the acquisition and masks. It is therewith possible to calculate or to specify both the display specifications themselves and the transformation given the presence of a specific image data set, at least in part without intervention of a medical-technical assistant or a doctor.

The image data set can already be adapted and/or displayed at least in part during the image acquisition and/or in a post-processing step after conclusion of the image acquisition. For example, in the generation of magnetic resonance exposures a standard orientation of the corresponding images (thus the associated image data already present) can already be achieved during the ongoing image acquisition using the slice positioning (which can be predetermined manually and automatically). Alternatively, it is possible to initially wait for the complete image data set acquisition and only then to effect the adaptation or representation, or to let the adaptation or, respectively, representation ensue later for a portion of the image data when, for example, this need not be used in order to make a decision about a directly-planned following examination or the further course of the examination.

The display specification can be stored in a databank (particularly an expandable databank). The use of a databank enables a simple search or a structuring for the case that a number of display specifications are stored for retrieval. An expansion capability with regard to the databank functionalities (such as fields and lists) thus can be assured, such that display specifications can be added for examination regions or organs not acquired previously or even new display specifications for organs for which a display specification is already stored in the databank.

The display specification and/or the representation instruction can appropriately be manually provided and/or changed at least in part by a user. It is thus possible for a user or even a user group to define its own display specifications, for example corresponding to the viewing standards selected for the image diagnosis which should be predominantly or generally maintained (followed) in a specific clinic or other medical facility. These specifications can vary from clinic department to clinic department or even can be predetermined individually by a specific doctor. The representation instruction for the transformation can likewise be determined or predetermined manually or also, if applicable, be appropriately changed by the user after a first automatic processing by the data processing device. Corrections of the automatic determination or also adaptations that appear suitable in the individual case for the diagnosis or evaluation thus can be effected.

Manual specifications and/or alterations can be evaluated by the data processing device and/or can be used for improvement of the display specifications. It is thus possible to extract user preferences using the effected changes or specifications in order to accordingly improve the automatically-determined display specifications or to further optimize the manual specifications. An intelligent system thereby arises that optimizes its usage in a specific medical apparatus in steps over the course of time, dependent on the user desires.

The display specification and/or the representation instruction that is used can be stored with image data set, particularly in the framework of a standard header. For example, such a standard header associated with image exposures presently specifies which organ or which examination region is shown in an image exposure in order to make the archiving of image exposures easier in the medical field. If the display specification (for example for a sagittal spinal column representation) is likewise stored in the header in addition to the representation instruction (which, for example, specifies the rotation angle and the translations), an already-existing archiving system with new functionalities is thereby used in accordance with the invention. The display specifications or representation instructions selected once are re-accessible at any time, such that the original image data set can be directly displayed without re-association of a display specification or a representation instruction.

A number of display specifications and/or representation instructions can be used and/or stored for an image data set. For example, for isotropic three-dimensional data sets, multiple pairs of display specifications and representation instructions can be stored, such as a standard header. Multiple display specifications can likewise be accessed, of which one may possibly be defined as the main display specification or the default display specification. Since no further specifications exist, this default display specification is then used as the standard for the image representation.

Furthermore, it is also possible to directly incorporate a number of display specifications into the checking of the image data set and the later adaptation and representation, such that multiple image series (corresponding to multiple display specifications for one image series) are simultaneously displayed to (for example) a medical-technical assistant on a monitor. Three-dimensional data sets can automatically be shown in all orientations that are relevant for the corresponding examination region without a manual adaptation (through an angle specification or a zoom or the like) being necessary. By the use of the standard header for specification of the display specification or representation instruction, this information is moreover accessible for different computer or software systems.

For image data sets representing multiple organs and/or anatomical regions, display specifications and/or representation instructions can be used for multiple organs and/or regions and/or be stored with the image data set. It is thereby ensured that a per-region, optimal representation can ensue in order to make the diagnosis easier given a subsequent image consideration. Every individual organ or, each examination region is shown in a matching standard orientation, such that the assessing doctor again recognizes the "normal" manifestation of the image, so an efficient evaluation is enabled. If multiple anatomical regions are equally acquired in the image data acquisition, a fast comparison capability for following studies or between exposures of different patients is ensured. It is in turn useful to store pairs of display specifications or representation instructions in a standard header.

Dependent on the display specification, a representation coordinate system can be defined, particularly with an origin and/or axis curve determined by at least one anatomical structure. For example, in an image data set of the knee, the tibial plateau can be defined as an origin of a representation coordinate system, whereby an axial plane through the meniscus is established and a sagittal plane proceeds perpendicular to the rear boundary of the condyle as well as parallel to the caudal-cranial direction of the tibia and of the femur. The section lines of the planes span the associated coordinate system as vectors.

The display specification can be integrated into an orientation format with regard to the entire body of the examination subject, particularly to establish a general whole-body coordinate system. A coordinate system with regard to the entire body can be established that is aligned on a specific orientation format of the human body and thus can be easily recognized or learned for a doctor or medical-technical assistant who is concerned with the image processing and evaluation.

The inspection of image exposures in the medical field is standardized with the inventive method in order to enable the capability of comparing different studies and even of exposures of different patients without problems. If display specifications and representation instructions are stored with the image data sets, these can thus be represented in one or more standardized orientations without further delay. For example, a default representation can be shown or display specifications corresponding to multiple standard orientations are used for image representation. Furthermore, a suitable orientation format can be defined using user specifications that, for example, are stored in a corresponding protocol. Through suitable image viewing software, the user can switch as needed between the representations of an image data set according to different representation specifications in order to effect an optimal evaluation.

DESCRIPTION OF THE DRAWINGS

FIGS. 2A-2E illustrate display specifications and representation instructions for an image data set of a spinal column in accordance with the inventive method.

DESCRIPTION OF THE PREFERRED EMBODIMENTS

Figure 1:
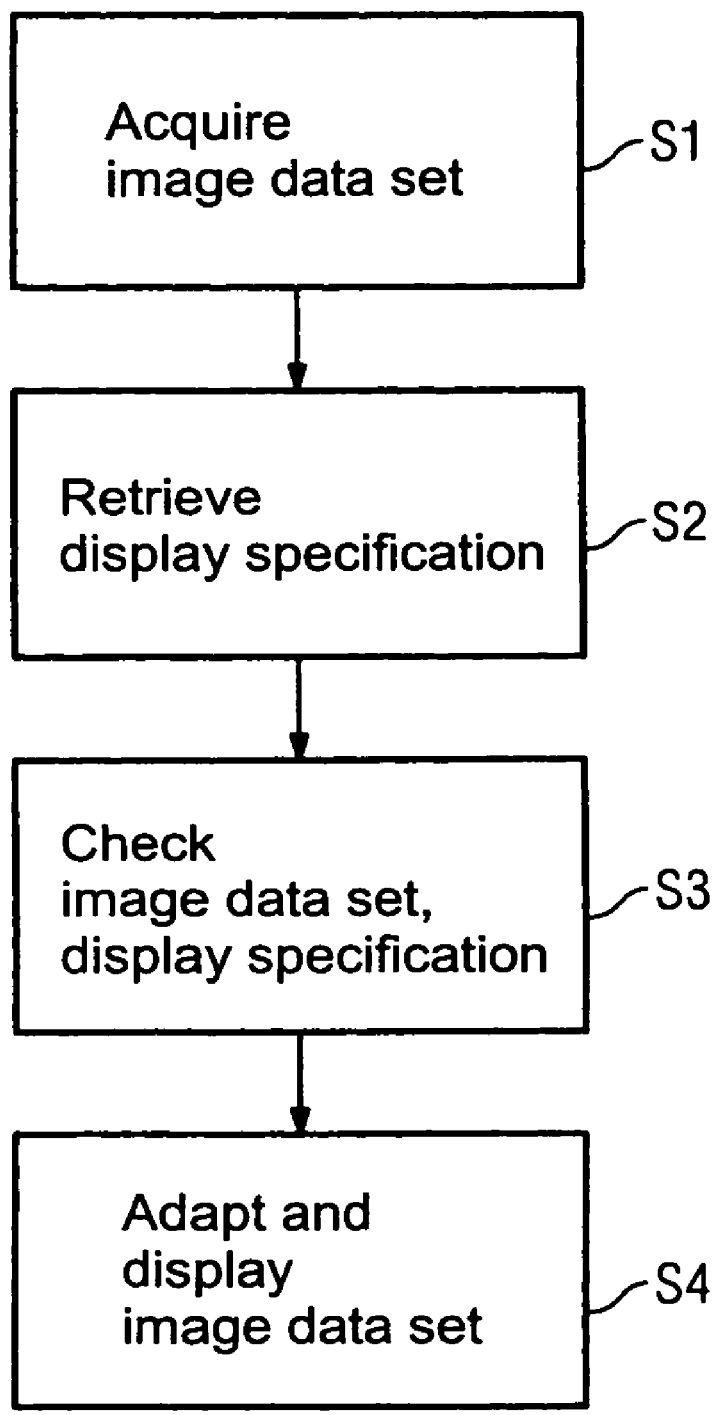
FIG. 1 is a flowchart of an embodiment of the inventive method.

FIG. 1 is a flowchart of an embodiment of the inventive method, in which initially an image data set of an examination region of an examination subject is acquired in a step S1 with an imaging medical imaging apparatus (in this case a magnetic resonance tomograph). Furthermore, a display specification that should be used for the subsequently-ensuing graphical representation of the acquired image data set is retrieved from a data processing device by a medical-technical assistant who conducts the image acquisition. This already ensues during the acquisition of the image data set in the step S2. The display specification (which is stored in a databank with further display specifications for various organs or examination regions) specifies an orientation to be maintained, for which further parameters that are important for the representation of the image exposures are provided in addition to a fundamental parameter that establishes that the region of interest is to be shown in the image center.

The image data set (insofar as it already exists) is finally checked in step S3 with regard to the display specification that is stored in the data processing device, whereupon the data processing device determines a representation instruction using the image content, the selected exposure series as well as the organ to be acquired under access to image processing techniques such as an edge detection and the like. This representation instruction specifies the coordinate transformations to be effected in order to arrive at a desired representation of the acquired image data. Values for the translations and rotations to be effected are determined for this purpose.

Finally, dependent on the check result (thus the calculated representation instruction), at least one part of the image data set is adapted in the step S4 and displayed corresponding the display specification. The display thereby ensues on a display such that, if applicable, the first image data can already be assessed during the examination. Further adaptations of errors of the representation instruction or with regard to a better medical assessment and evaluation can be manually effected by the user in that he correspondingly alters the representation instruction.

Further representations of the image data sets according to other standard orientations are displayed according to a corresponding selection of an option provided by a representation software, such that the user can switch back and forth between these individual representations.

In the inventive method, an acquired image data set is thus shown according to default predetermined orientation schemata that can be easily learned by a user and ensure a comparison capability for subsequent examinations of the patient or other patients.

Examples regarding display specifications and representation instructions given an image data set of a spinal column are shown in FIGS. 2A-2E.

FIG. 2A shows a representation of the spinal column of a person according to a display specification regarding a standard orientation. According to this display specification the spinal column is arranged in the image center, whereby it is shown in the caudal-cranial direction. This standardized representation allows a simple comparison capability with later exposures that are acquired with different modalities or, respectively, in a greater time interval. By contrast, FIG. 2B shows an image data set that does not satisfy these display specifications; here the spinal column is arranged outside of the center and running at an angle relative to the image. Such an image data set that satisfies no display specification but rather is determined only by the type and manner of the image acquisition makes a qualitatively high-grade diagnosis difficult since the representations is unfamiliar for the evaluating medical-technical assistant or doctor. Under the circumstances, it can even lead to misdiagnoses, whereby generally the comparison capability with subsequently-acquired image exposure series or reference series is not provided. Should series of exposures be compared that (like the spinal column shown in FIG. 2B) are displayed without display specification, the assistant or doctor entrusted with the evaluation must initially, laboriously find corresponding exposures.

Corresponding sagittal or coronal views of the spinal column are shown in FIG. 2C as well as 2D, whereby here individual slices through the intervertabral discs are indicated with parallel lines. A representation instruction that specifies the transformation that leads from the original image data set to the desired representation of FIG. 2E can thus be determined using a display specification for the lumbar spinal column that leads to a representation as it is shown in FIG. 2E. A display specification for the spinal column that states that a transversal view is desired is thus indicated for FIGS. 2C and 2D, as indicated by the sections, whereby the representation plane should proceed parallel to the intervertabral disc (thus twice as angled). In the transversal view of FIG. 2E, the spinal column (designated in Figures with the reference character 1) is thus shown with the intervertabral discs 2 corresponding to the lines 3 that predetermine the sections. A vertebra 1*a* is hereby to be viewed, whereby the representation runs parallel to the intervertabral disc. The slice center is indicated by a circle 4, and this is positioned in the image center such that an optimal image evaluation and finding is enabled. The original image data set to which the FIG. 2E returns is stored with the display specification used and the calculated representation instructions, such that the representation can be quickly retrieved at any time, for example for comparison with the exposures of a subsequent examination.

Figure 3A:
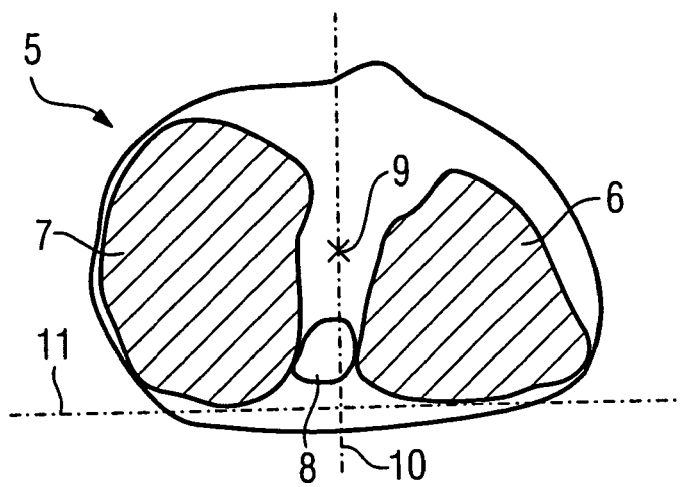
FIGS. 3A and 3B illustrate a representation coordinate system for the knee region in accordance with the invention.
Figure 3B:
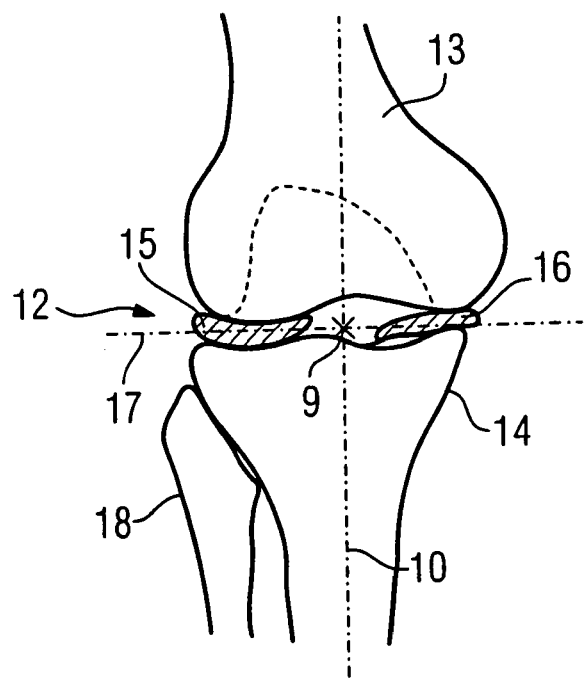

FIGS. 3A and 3B exemplify the definition of a representation coordinate system for the knee region.

A view from above of the joint area 5 of the tibia is shown in FIG. 3A. The representation of FIG. 3A follows a display specification with regard to the orientation to be maintained of an acquired image data set. The lateral condyle 6 as well as the medial condyle 7 of the tibia is visible. A protuberance 8 (what is known as the eminentia intercondylaris (intercondylar eminence) is located between the two condyles. The standardized representation of the joint surfaces 5 of the tibia, as it is shown in FIG. 3A, is now used to define a representation coordinate system for the knee region. This coordinate system is characterized in that the coordinates exhibit an anatomical meaning in this coordinate system.

The geometric center of the tibial plateau is established as an origin 9 of the representation coordinate system. The sagittal plane 10 proceeds through the origin 9 of the coordinate system, perpendicular to the rear boundary of the condyles and parallel to the head-foot direction of the tibia and the femur. The coronal plane 11 (likewise plotted) runs parallel to the rear boundary of the condyles and along the caudal-cranial foot direction of the tibia and the femur.

Dependent on a display specification, a representation coordinate system is defined that allows an anatomical association via the origin 9 as well as the curve of the sagittal plane 10 and of the coronal plane 11 with regard to the knee region to be represented.

In FIG. 3B, the knee 12 is additionally shown from the front in a view corresponding to a display specification. Here the anatomically-significant origin 9 of the coordinate system is also visible again. The menisci (namely the lateral meniscus 15 and the medial meniscus 16) are arranged between the femur 13 and the tibia 14. Furthermore, here the still-missing axial plane 17 (which is defined by the menisci 15, 16) is shown in addition to the sagittal plane 10. The fibula 18 is likewise indicated.

In the inventive method, the standardized orientations are thus used as display specifications for definition of a representation coordinate system that allows a comparably simple specification of coordinates since these are established by the significant anatomical structures of the respective acquired examination region. A coordinate specification with regard to this representation coordinate system (which, for example, has the coordinates 40, 0 and 3) can accordingly be interpreted such that a point is meant that is located 40 mm lateral to the center line of the knee in the anterior-posterior center of the knee and thereby lies 3 mm above the tibial plateau.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating on a medical image data set, comprising the steps of:
   acquiring a medical image data set of an examination region of a subject by interaction with the subject using a medical imaging apparatus;
   from a data processing device in which a display specification, describing an orientation for a graphical representation of said image data set, is electronically stored, retrieving said display specification;
   in the data processing device, automatically electronically checking said image data set with respect to said display specification, to obtain a check result; and
   automatically electronically adapting said image data set as needed to conform said image data set to said display specification dependent on said check result, and visually displaying at least a part of said image data set at a display device with the graphical representation described by said display specification.

2. A method as claimed in claim 1 comprising storing said display specification in said data processing device as a display specification selected from the group consisting of a display specification specific to said examination region, and display specifications respectively specific for an anatomical organ in said examination region.

3. A method as claimed in claim 1 comprising storing a plurality of image representation parameters as said display specification in said data processing device, comprising a basic display representation parameter and at least one supplementary display representation parameter.

4. A method as claimed in claim 1 comprising storing a plurality of different display specifications in said data processing device respectively specific to different examination regions.

5. A method as claimed in claim 1 wherein said display unit comprises a screen with a representation region, and comprising storing, as said display specification in said data processing device, a display specification that centers an anatomical region of interest in said examination region with respect to said representation region of said screen.

6. A method as claimed in claim 1 wherein the step of adapting said image data set to conform to said display specification comprises specifying a coordinate transformation relationship between first coordinates of said image data set acquired with the medical imaging apparatus and second coordinates for displaying said medical image data set at said display device, and transforming said medical image data set from said first coordinates to said second coordinate.

7. A method as claimed in claim 1 comprising, in said data processing device, automatically determining said display specification using a determination procedure selected from the group consisting of examination region-specific algorithms, anatomical organ-specific algorithms, medical imaging apparatus-specific algorithms, image processing algorithms, and predetermined rules.

8. A method as claimed in claim 1 comprising adapting said medical image data set to conform to said display specification at least in part during acquisition of said medical image data set with said medical imaging apparatus.

9. A method as claimed in claim 1 comprising adapting said medical image data set to conform to said display specification in a post-processing procedure after acquisition of said medical image data set with said medical imaging apparatus.

10. A method as claimed in claim 1 comprising storing said display specification in a data bank accessible by said data processing apparatus.

11. A method as claimed in claim 10 comprising storing said display specification in a data bank that is expandable in terms of storage capacity.

12. A method as claimed in claim 1 comprising allowing at least one of selection and modification of said display specification via a manual entry made through a user interface of said data processing device.

13. A method as claimed in claim 12 comprising permanently modifying a display specification according to said manual entry, and storing the modified display specification for subsequent use with a subsequently-acquired medical image data set.

14. A method as claimed in claim 1 comprising electronically storing said display specification together with said medical image data set.

15. A method as claimed in claim 14 comprising storing said display specification as a header for said medical image data set.

16. A method as claimed in claim 14 comprising storing multiple display specifications together with said medical image data set.

17. A method as claimed in claim 16 wherein said medical image data set comprises data representing a plurality of components, selected from the group consisting of anatomical organs and examination sub-regions, and storing said medical image data set together with multiple display specifications respectively for said components.

18. A method as claimed in claim 1 comprising storing a display specification defining a coordinate system determined by at least one anatomical structure in the examination region, and displaying said medical image data set according to said coordinate system in said display specification.

19. A method as claimed in claim 18 comprising defining said coordinate system using a coordinate system origin and at least one coordinate system axis proceeding through said origin.

20. A method as claimed in claim 18 comprising employing a coordinate system in said display specification that is integrated into a generalized whole-body coordinate system for said subject.

* * * * *